United States Patent [19]
Mikkelsen

[11] Patent Number: 5,984,900
[45] Date of Patent: Nov. 16, 1999

[54] AUTOMATIC PEN-SHAPED SYRINGE

[75] Inventor: Søren Mikkelsen, Ballerup, Denmark

[73] Assignee: Novo Nordisk A/S, Bagsvaerd, Denmark

[21] Appl. No.: 08/256,883

[22] PCT Filed: Nov. 30, 1992

[86] PCT No.: PCT/DK92/00358

§ 371 Date: May 20, 1994

§ 102(e) Date: May 20, 1994

[87] PCT Pub. No.: WO93/10838

PCT Pub. Date: Jun. 10, 1993

[30] Foreign Application Priority Data

Nov. 29, 1991 [DK] Denmark .................................. 1942/91

[51] Int. Cl.$^6$ .................................................. A61M 5/00
[52] U.S. Cl. .......................... 604/208; 604/135; 604/136; 604/157; 604/232
[58] Field of Search ..................... 604/232–234, 604/207–209, 135, 131, 136, 132–134, 117, 218, 137–139, 199, 220, 71, 72, 156, 157

[56] References Cited

U.S. PATENT DOCUMENTS

| | | | |
|---|---|---|---|
| 4,865,591 | 9/1989 | Sams | 604/211 |
| 4,936,833 | 6/1990 | Sams | 604/232 |
| 4,973,318 | 11/1990 | Holm et al. | 604/208 |
| 5,092,842 | 3/1992 | Bechtold et al. | 604/209 |
| 5,114,406 | 5/1992 | Gabriel et al. | 604/136 |
| 5,226,895 | 7/1993 | Harris | 604/208 |
| 5,226,896 | 7/1993 | Harris | 604/208 |
| 5,244,465 | 9/1993 | Michel | 604/232 |

FOREIGN PATENT DOCUMENTS 2040076  8/1970  Germany .

*Primary Examiner*—Ronald Stright, Jr.
*Attorney, Agent, or Firm*—Steven T. Zelson, Esq.

[57] ABSTRACT

A pen shaped syringe with automatic needle insertion has an injection system integrally displaceable in a housing and comprising a basic part carrying a medicine reservoir with a hypodermic needle at its distal end, and a dosing mechanism with a carrier engaging a cogged piston rod, the carrier being coupled to a dose spindle in a rotatable but not displaceable way. The dose spindle is provided with a thread engaging a thread in a sequence part having protrusions engaging slots in the basic part to allow a limited axial movement of the parts in relation to each other, the extent of the movement being defined by the rotational position of the dose spindle. A spring is compressed between the basic part and the housing when the basic part is moved in the proximal direction by exerting a cocking force on the sequence part which part after having performed the set limited axial movement in relation to the basic part carries this basic part against the force of the spring.

4 Claims, 2 Drawing Sheets

AUTOMATIC PEN-SHAPED SYRINGE

BACKGROUND OF THE INVENTION

The invention relates to pen-shaped syringes with automatic needle insertion, which syringes have an injecting system comprising a basic part carrying a medicine reservoir being at its distal end provided with a hypodermic needle and being at its proximal end closed by a piston, a dosing mechanism having a carrier engaging a cogging on a piston rod to advance this rod in the distal direction to press the piston into the reservoir a distance corresponding to a set dose when an injection button is pressed, the injection system being integrally displaceable in a housing by a spring which may be compressed and released to displace the injection system in the distal direction in the housing to insert the needle into the skin of a patient.

Such pen shaped syringes are used by patients who treat themselves by frequently injecting a medicine dose which may be set individually immediately before each injection, and the setting is deleted when the injection is performed. Often the same dose is used by a number of injections, and consequently some patients might wish for a syringe by which the dose does not have to be set before each injection. Especially patients to whom a reduced tactile motor function makes it difficult to perform the setting would appreciate a syringe by which a setting is not deleted by the injection, but is remembered until it is altered voluntarily.

SUMMARY OF THE INVENTION

It is the object of the invention to provide a syringe with automatic needle insertion, which syringe stores a setting of the dose and automatically sets that dose when the automatic needle insertion mechanism of the syringe is cocked.

This is obtained by a pen shaped syringe as described above, which syringe according to the invention is characterized in, that the carrier is coupled to a dose spindle in a rotatable but not displaceable way, the dose spindle being provided with a thread engaging a thread in a sequence part, the sequence part and the basic part of the injection system being provided with mutually engaging protrusions and slots allowing a set limited axial movement of these parts in relation to each other, the basic part being affected by a spring mounted to be compressed when the basic part is moved in the proximal direction in the housing by cocking forces exerted on the sequence part.

According to the invention, a ramrod may be mounted displaceably axially in the housing with an outer end accessible for operating the ramrod, and an inner end abutting a protrusion on the sequence part. Thereby it is ensured that the cocking force is exerted on the sequence part.

When the injection button has a diameter at least corresponding to the minor diameter of the housing and is secured to the dose tube at the proximal end of the syringe, this button may be gripped easily, even by patients with reduced tactile motor function, and by drawing the button in the proximal direction the force exerted on the button may via the dose spindle and the thread engaging the thread of the sequence part be transmitted to this part as a cocking force.

BRIEF DESCRIPTION OF THE DRAWINGS

In the following the invention is described in further details with reference to the drawing, wherein.

DETAILED DESCRIPTION OF THE INVENTION

Figure 1:
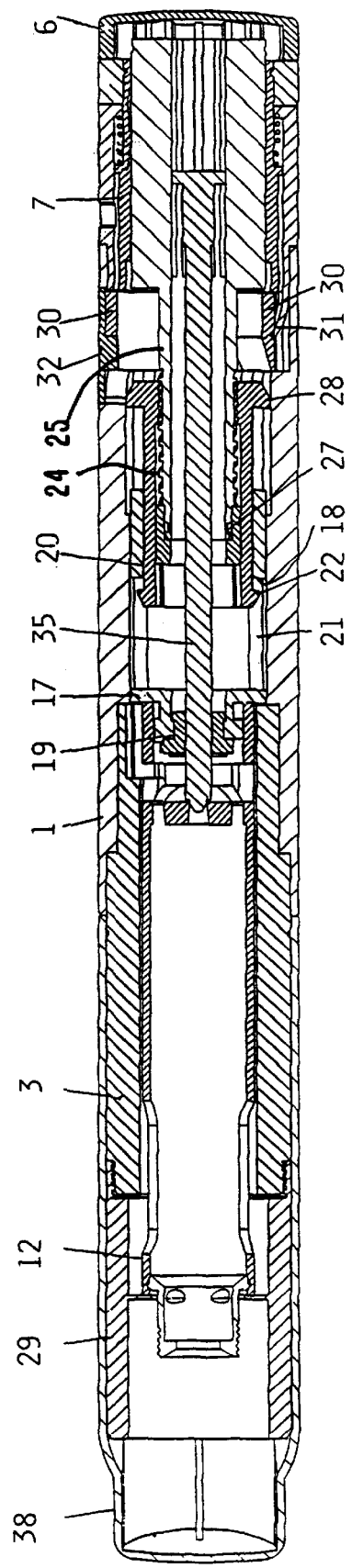
FIG. 1 shows a sectional view along the axis of a pen-shaped syringe according to the invention.
Figure 2:
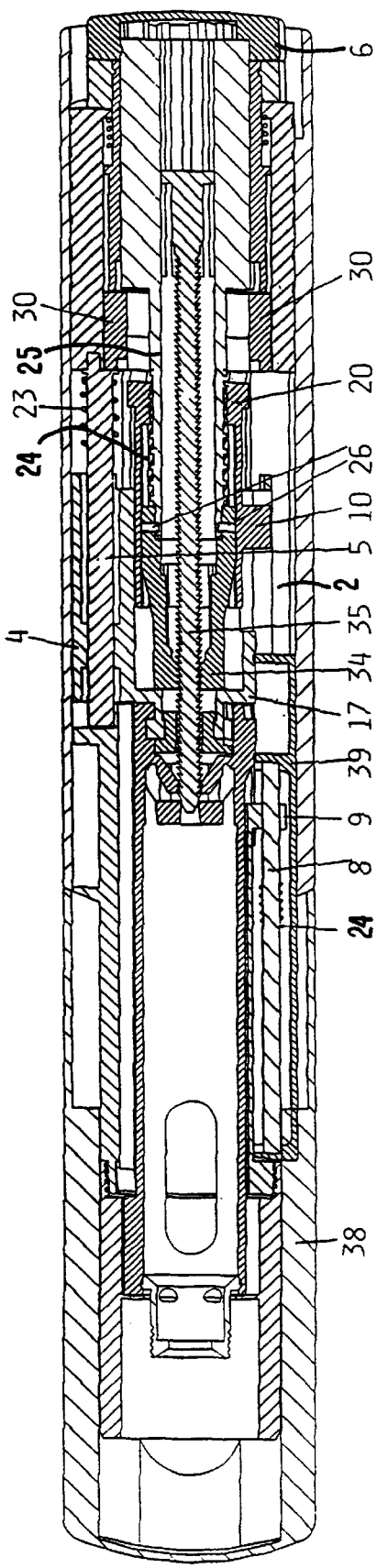
FIG. 2 shows a sectional view along the axis of the syringe in FIG. 1 perpendicular to the view in that Figure.

The pen shaped syringe with an automatic insertion of a needle shown in FIGS. 1 and 2 in its uncocked position comprises a housing 1 having an oval cross section and with a bore accommodating the mechanism for automatic needle insertion, dose setting, and injection. Partly inserted into the distal end of the housing 1 an intermediate tube 3 extends from this housing. At the outer end of the intermediate tube 3 a spacing tube 29 is mounted, which spacing tube 29 determines the depth of the needle insertion. An injecting system comprising a basic part 17 and a tubular reservoir holding member 12 is accommodated axially displaceably in the housing 1 and the intermediate tube 3. The tubular reservoir holding member 12 is releasably secured to the basic part 17 by a bayonet coupling.

The reservoir holding member 12 accommodates a reservoir for the medicine to be injected and carries at its distal end a hub with a hypodermic needle. The basic part 17 is the element on which the cartridge is mounted and which surrounds the carrier and the sequence part. The basic part is made unrotatable in the housing by having a side projection 4 with a bore by which it is guided along a guiding bar 5 in the housing. The guiding bar 5 is further surrounded by a helical spring 23 compressed between the housing and the side projection 4 to urge this projection, and consequently the basic part 17 and the member 12 in a distal direction in the housing.

A mainly tubular sequence part 20 is displaceable in the basic part 17 within limits set by hooks 22 extending into slots 21 in the sides of the basic part 17. The sequence part ensures that the syringe is prepared to inject a set dose prior to the cocking of the needle insertion spring. This also is a two step process, during the first step the sequence part is moved bringing the carrier with it so that this carrier is clicking over a number of teeth on the piston rod, and during the second step the needle insertion mechanism is cocked as the hooks 22 of the carrier abuts the surface 18 on the basic part and moves it in a proximal direction so the the tubular projection 4 on the basic part compresses the spring 23 which supplies the energy for the automatic needle insertion. At its proximal end, the sequence part 20 is provided with an internal thread engaged by an external thread 24 on a dose setting spindle 25. At its proximal end, the dose setting spindle is provided with a button 6 which may be rotated to set a dose before the needle insertion mechanism is cocked, and be pressed to inject the set dose when the needle has been inserted into the skin of the patient. This button has a diameter corresponding to the minor diameter of the housing and is along its outer cylindric surface provided with grooves to provide for a good grip for the fingers when the button shall be rotated.

A piston rod 35 having a mainly square cross section and being cogged along two opposite sides and smooth along the other two sides is during its normal use maintained unrotatable in the housing by being guided through a piston rod guide 19. The cogging is engaged by a carrier 34 which is mounted to the distal end of the dose setting spindle 25 by a hair pin shaped locking pin engaging slots 26 in the carrier 34 and an annular recess 27 at the end of the spindle 25. By this arrangement, the spindle 25 may be rotated in relation to the carrier 34, but the carrier will follow axial movements of the spindle. Further, the carrier 34 is guided in the sequence part 20 to be unrotatable in relation to this part and consequently in relation to the housing.

When the syringe is in its neutral uncocked position, as shown in FIGS. 1 and 2, the set dose is determined by the distance of the hooks 22 of the sequence part 20 from the proximal terminal surfaces 18 of the slots 21 in the basic part 17. This distance may be adjusted by rotating the button 6 to rotate the spindle 25. Due to its engagement with the thread of this spindle and its unrotatable guidance in the basic part 17 the sequence part 20 will travel along the spindle altering its position in the basic part. The set dose may be read from not shown digits along the outer surface of a drum 7 coupled to the button 6 to follow the rotational position of this button, but without being axially displaced in the housing. The rotational position of the drum 7 is indicated by a digit appearing in a window in the wall of the housing.

The syringe is cocked by actuating the sequence part in the proximal direction. By this actuating the button is lifted from the end of the housing due to the thread connection between the sequence part 20 and the spindle 25, and the spindle 25 will draw the carrier in the proximal direction making its teeth ride over the teeth of the cogging of the piston rod 35. When the hooks 22 reach the terminal surfaces 18 of the slots 21, the basic part 17 will follow the sequence part 20 in its further displacement in the proximal direction, and the helical spring 23 will be compressed. As now the whole injection system is displaced, no further relative movement of the carrier and the piston rod is performed, and this relative movement has consequently been restricted to the movement defined by the original distance established between the hooks 22 and the surfaces 18 by setting the dose.

When the sequence part 20 is passed in the proximal direction, a flange 28 provided at its proximal end will pass through a trigger ring 30 which is pushed to an eccentric position by a leaf spring 31. When passing the trigger ring 30 the flange 28 will incidently against the force of the leaf spring 31 push the trigger ring into a position coaxial with the housing, and when the flange has passed the spring 31 will again push the trigger ring 30 to its eccentric position, and movement of the sequence part in the distal direction will be locked by the flange abutting the proximal side of the trigger ring 30.

Now the distal end of the spacing tube 29 is pressed against the skin where an injection shall be given. A trigger button 32 is pressed, and the trigger ring 30 is thereby pushed out of its eccentric position into a position coaxial with the housing. Thereby the locking engagement between trigger ring 30 and the flange 28 of the sequence part is released, and the spring 23 can push the basic part 17 in the distal direction. Thereby the needle mounted at the distal end of the member 12 is pressed through the skin of the patient and is ready for injection. During its movement in the distal direction the basic part 17 draws the sequence part with it due to the hooks 22 engaging the surface 18. The movement of the basic part is stopped by abutting the end of the intermediate tube 3. The position of the sequence part 20 is now as at the beginning of the loading when the compression of the spring 23 has not yet begun, i.e. the button is lifted over the end of the syringe a distance corresponding to the set dose. This dose may now be injected by pressing the button until it abuts the end of the syringe. By this pressing the carrier 34 will carry the piston rod 35 in the distal direction, and the piston rod will press the piston further into the ampoule and press out some of the content of this ampoule through the needle. The carrier is the element which when moved during the injection transmits its movement to another element, the piston rod. i.e. carries this element along.

The cocking actuation of the sequence part in the proximal direction may be obtained by pulling the button 6 and the spindle 25, which due to its thread engagement with the sequence part 20 will draw this part with it. Alternatively, the cocking may be performed by operating a ramrod 39 adjacent to the outer wall of the intermediary tube 3 and displaceably in the axial direction thereof in a bore in the housing. To cock the needle insertion mechanism the ramrod 39 is pressed into the bore 2 in the housing 1 against the force of a retraction spring 44 surrounding a guiding bar 8 in the ramrod 39 and being compressed between an end of the ramrod and a ramrod guide 9 on the intermediary tube 3. When pressed into the housing 1 the ramrod 39 will engage a protrusion 10 on the sequence part, and further pressing of the ramrod will cause the actuation of the sequence part in the proximal direction.

Figure 3:
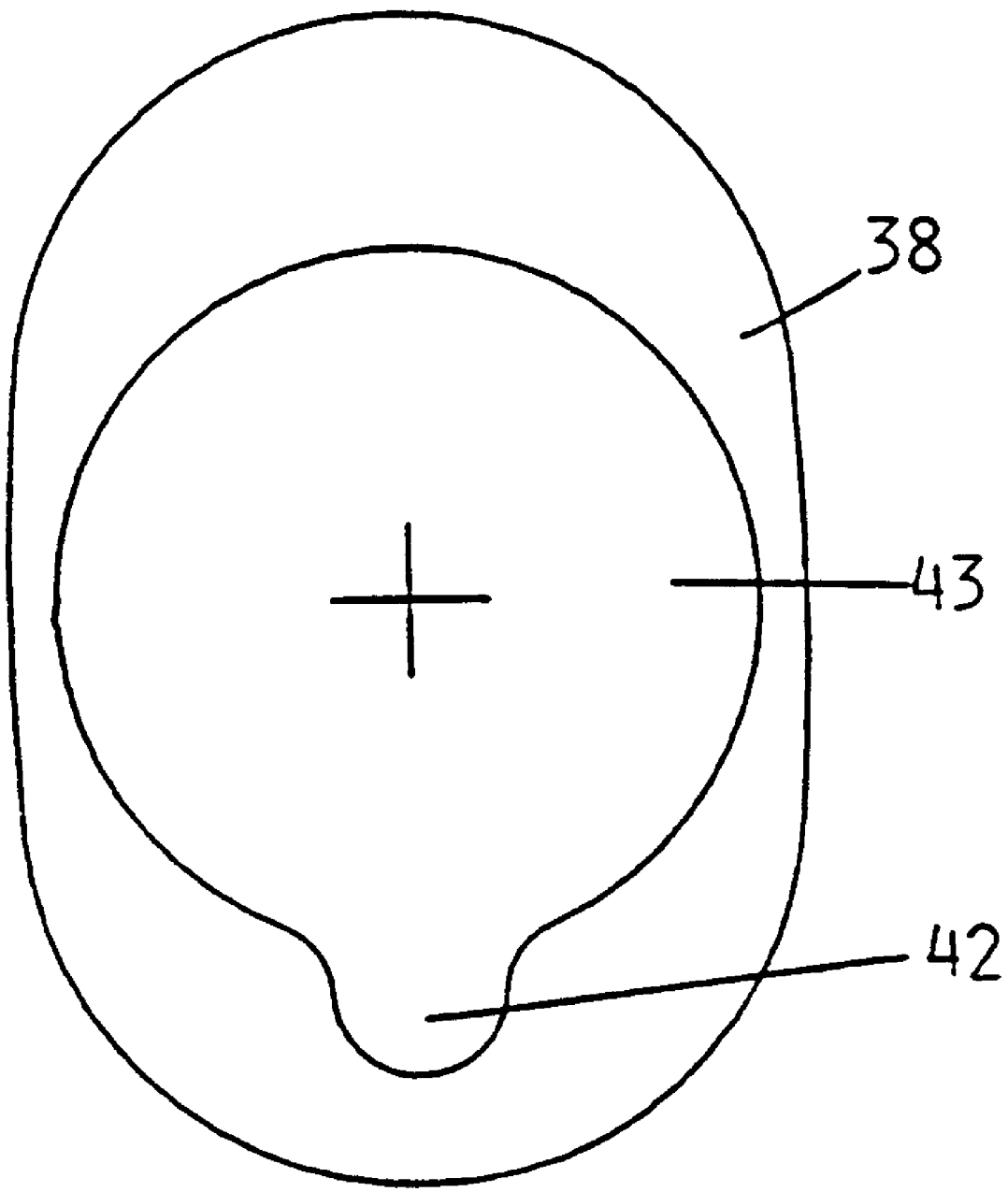
FIG. 3 shows a protective cap seen from its proximal end.

A protective cap 38 having the same cross section as the housing 1 has a bore 43 fitting over the protruding end of the intermediary tube 3. The inner wall of the cap further has a longitudinal recess 42 accommodating the ramrod 39. FIG. 3 shows the cap seen from its open end. If the cap 38 is pulled off so far that the ramrod 39 is free it may be rotated about the intermediate tube 3 and the spacing tube 29. Thereby the cap may be used for operating the ramrod which now abuts the proximal edge of the cap 38, which cap guided on the intermediate tube provides a handle by which the ramrod may be pressed into the housing 1.

I claim:

1. A pen-shaped syringe which may be used for automatic insertion of a needle and subsequent injection of a set dose, said syringe comprising a housing having an axis and proximal and distal ends, and:

(a) a basic part which is axially displaceable in the housing;

(b) a medicine holding member, disposed in said housing, which is coupled to the basic part to follow axial movements of the basic part, which has a proximal end and a distal end, and which is designed to carry an injection needle at its distal end;

(c) a spring coupled between said basic part and said housing for urging said basic part towards the distal end of said housing;

(d) a piston rod provided with cogging, wherein said piston rod is axially movable within said housing and has a distal end adjacent the proximal end of said medicine holding member;

(e) a dose setting spindle having a distal end which is disposed in the housing and which is provided with an outer thread and a proximal end terminated by a button disposed outside of said housing for setting a dose, wherein said spindle is both rotatable about the housing axis and axially displaceable relative to the housing;

(f) a carrier disposed in said housing, which carrier is coupled to the dose setting spindle to follow axial movements of the spindle and which carrier engages the cogging of the piston rod in such a way that, when the carrier is moved in a proximal direction, the carrier slides over the cogging, and, when the carrier is moved in a distal direction, the carrier moves the piston rod with it; and (g) a sequence part which is axially displaceable but non-rotatable in the housing, which sequence part has a proximal end with an internal thread engaging the outer thread of the dose setting spindle, such that rotation of the spindle, due to the non-rotatability of the sequence part, moves the sequence part in the axial direction;

wherein one of the said base and sequence parts includes an axially oriented slot having a terminal surface, and the other of the said base and sequence parts includes a first protrusion disposed in the slot for selectively engaging the terminal surface;

wherein a dose may be set by rotating the spindle such that the protrusion is moved a predetermined distance away from the terminal surface;

wherein the syringe may be cocked by moving the sequence part axially towards the proximal end of the housing, wherein initial movement of the sequence part causes the protrusion and the terminal surface to move towards one another without movement of the basic part in the housing, and wherein, after the protrusion engages the terminal surface, further movement of the sequence part moves the basic part, against the force of the spring, along with the holding member, in the proximal direction, which will retract a needle mounted on the holding member into the housing;

wherein, upon releasing the sequence part, the spring moves the basic part and, along with it, the holding member, sequence part, and spindle, towards the distal end of the housing, whereby a needle mounted on the holding member will protrude from the distal end of the housing; and wherein the predetermined dose may then be administered by pushing the spindle in the distal direction.

2. A pen-shaped syringe according to claim 1, wherein the protrusion is provided on the sequence part, and the slot is provided in the basic part.

3. A pen-shaped syringe according to claim 2, further comprising a ramrod which is axially displaceable relative to the housing, wherein the ramrod includes a first portion which is accessible from outside the housing for moving the ramrod axially, and wherein the ramrod abuts the sequence part such that, when the ramrod is moved in a proximal direction, such movement is transmitted to the sequence part for moving the sequence part in a proximal direction.

4. A pen-shaped syringe according to claim 1, further comprising a trigger means supported by the housing which, after a predetermined axial movement of the sequence part in the proximal direction, prevents movement of the sequence part in a distal direction, and a trigger release which, when actuated, causes the trigger means to release the sequence part.

* * * * *